(12) United States Patent
Fankhauser

(10) Patent No.: US 9,217,122 B2
(45) Date of Patent: Dec. 22, 2015

(54) CYCLODODECADIENONE DERIVATIVES AS PERFUMING INGREDIENTS

(75) Inventor: Peter Fankhauser, Geneva (CH)

(73) Assignee: Firmenich SA, Geneva (CH)

( * ) Notice: Subject to any disclaimer, the term of this patent is extended or adjusted under 35 U.S.C. 154(b) by 119 days.

(21) Appl. No.: 14/126,484

(22) PCT Filed: Jun. 18, 2012

(86) PCT No.: PCT/EP2012/061554
§ 371 (c)(1),
(2), (4) Date: Dec. 16, 2013

(87) PCT Pub. No.: WO2012/175437
PCT Pub. Date: Dec. 27, 2012

(65) Prior Publication Data
US 2014/0135402 A1    May 15, 2014

(30) Foreign Application Priority Data

Jun. 22, 2011 (EP) .................................. 11170895

(51) Int. Cl.
| | | |
|---|---|---|
| *C11B 9/00* | (2006.01) | |
| *A61K 8/35* | (2006.01) | |
| *A61Q 13/00* | (2006.01) | |
| *C11D 3/50* | (2006.01) | |
| *A61Q 5/02* | (2006.01) | |
| *A61Q 5/06* | (2006.01) | |
| *A61Q 15/00* | (2006.01) | |
| *A61Q 19/00* | (2006.01) | |
| *C07C 49/607* | (2006.01) | |

(52) U.S. Cl.
CPC .................. *C11B 9/0038* (2013.01); *A61K 8/35* (2013.01); *A61Q 5/02* (2013.01); *A61Q 5/06* (2013.01); *A61Q 13/00* (2013.01); *A61Q 15/00* (2013.01); *A61Q 19/002* (2013.01); *C07C 49/607* (2013.01); *C11D 3/50* (2013.01)

(58) Field of Classification Search
USPC ............................................................ 512/8
See application file for complete search history.

(56) References Cited

U.S. PATENT DOCUMENTS

| | | | |
|---|---|---|---|
| 3,128,304 A | | 4/1964 | Lafont et al. |
| 4,885,397 A | * | 12/1989 | Bueschken .................. 568/341 |
| 4,990,495 A | * | 2/1991 | Giersch et al. .................. 512/8 |
| 2010/0190869 A1 | | 7/2010 | Teles et al. |

FOREIGN PATENT DOCUMENTS

| | | | |
|---|---|---|---|
| EP | 0 115 582 A2 | 8/1984 | |
| EP | 0 965 575 A1 | 12/1999 | |

OTHER PUBLICATIONS

International Search Report and Written Opinion, application PCT/EP2012/061554, mailed Sep. 3, 2012.

* cited by examiner

*Primary Examiner* — Ling Choi
*Assistant Examiner* — Lanee Reuther
(74) *Attorney, Agent, or Firm* — Winston & Strawn LLP

(57) ABSTRACT

The present invention relates to compounds of Formula (I), wherein one R group is a hydrogen atom and the other is a hydrogen atom or a $C_{1-3}$ alkyl group; and each carbon-carbon double bond of said compound, independently from each other, can be in a configuration Z or E or a mixture thereof; which are useful perfuming ingredients.

(I)

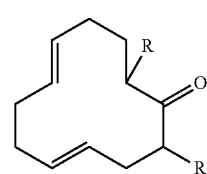

16 Claims, No Drawings

CYCLODODECADIENONE DERIVATIVES AS PERFUMING INGREDIENTS

TECHNICAL FIELD

The present invention relates to the field of perfumery. More particularly, it concerns the use as perfuming ingredient of derivatives of formula (I) as defined below. The present invention also comprises the composition wherein the invention's compound is part of a perfuming composition or of a perfuming consumer product.

PRIOR ART

To the best of our knowledge, in general terms 4,8-cyclododecadien-1-one is a known compound which has been described in the literature, but only as chemical intermediate. For instance, one may cite EP 965575 wherein is disclosed a 87/12 mixture of (Z,E)-4,8-cyclododecadien-1-one and (E,Z)-4,8-cyclododecadien-1-one as starting material for the preparation of 1-(4,8-cyclododecadien)-2-methyl-1-propanone as perfuming ingredient. One may also cite US 2010/0190869 wherein 4,8-cyclododecadien-1-one is obtained as intermediate in the synthesis of perfuming aldehydes. However, these prior art documents do not report or suggest any organoleptic properties of the present invention's mixture of formula (I), or any use of said compounds in the field of perfumery.

U.S. Pat. No. 4,885,397 also discloses the preparation inter alia of 4,8-cyclododecadien-1-one, as intermediate for the preparation of a number of other chemicals. Said document states clearly that only the $C_{15-17}$ ketones are useful as perfuming ingredient, to the contrary of what has been found in the present invention.

To the best of our knowledge, the compounds of formula (I), wherein A is other than a carbonyl, are not reported in the literature.

The perfumery industry knows cyclododec-2-enone as perfuming ingredient to impart patchouli oil notes (e.g. EP 115582), but this compound possesses a significantly different skeleton (i.e. the macrocycle comprises a conjugated enone functionality) and odor from the one of the present invention. The closest known analogues of the invention's compounds are 5,9-cyclododecadien-1-ol (see U.S. Pat. No. 3,128,304) or some α alkoxy cyclododecadienones (see U.S. Pat. No. 4,990,495) but once again these compounds are significantly different (an alcohol or α-alkoxy-ketone versus a ketone) and have different odors as discussed below. Further below in Table 1 are highlighted the differences between the invention's compounds and the prior art compounds.

These prior art documents do not report or suggest any organoleptic properties of the compounds of formula (I), and do not report or suggest any use of said compounds in the field of perfumery.

DESCRIPTION OF THE INVENTION

We have now surprisingly discovered that a 4,8-cyclododecadien-1-one derivative of formula

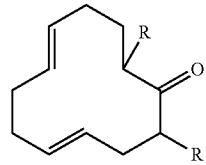

(I)

wherein one R group is a hydrogen atom and the other is a hydrogen atom or a $C_{1-3}$ alkyl group; and
each carbon-carbon double bond of said compound, independently from each other, can be in a configuration Z or E or a mixture thereof;
can be used as perfuming ingredient, for instance to impart odor notes of the woody type with aromatic, musky, and/or earthy type.

For the sake of clarity, by the expression "a compound of formula (I) . . . each carbon-carbon double bond of said compound, independently from each other, can be in a configuration Z or E or a mixture thereof", it is meant also a composition of matter comprising the various (E,E), (E,Z) or (Z,E) and (Z,Z) isomers of 4,8-cyclododecadien-1-one, 12-methylcyclododeca-4,8-dienone and/or 2-methylcyclododeca-4,8-dienone.

According to any one of the above embodiments of the invention, one R group is a hydrogen atom and the other is a hydrogen atom or a methyl or ethyl group. In particular both R represent a hydrogen atom.

For the sake of clarity, by the expression "each carbon-carbon double bond of said compound, independently from each other, can be in a configuration Z or E or a mixture thereof" it is meant the normal meaning in the art, i.e. that said compound (I) can be in the form of an essentially pure stereoisomer (i.e. the (4E,8E) one) or in the form of a mixture of stereoisomers, e.g. in a mixture comprising the stereoisomers (4E,8E), (4Z,8E) and (4E,8Z) in various w/w ratios.

In particular, the invention's compound can be in the form of a mixture containing predominantly the stereoisomers (4E,8E), (4Z,8E) and (4E,8Z), the remaining being essentially the (4Z,8Z) stereoisomer. In such a case, one may define a w/w ratio (4E,8E)/[(4Z,8E)+(4E,8Z)] for such mixture of stereoisomers (also referred to as the (E,E)/((E,Z) ratio). According to a particular aspect of said embodiment, the compound (I) is in the form of a mixture of stereoisomers having a (E,E)/((E,Z) ratio comprised between 20/80 and 1/99. According to said embodiment, said mixture of stereoisomers has a (E,E)/((E,Z) ratio comprised between 15/85 and 2/98.

Alternatively said compound (I) is in the form of a mixture of stereoisomers having a (E,E)/((E,Z) ratio comprised between 80/20 and 99.5/0.5. According to said embodiment, said mixture of stereoisomers has a (E,E)/((E,Z) ratio comprised between 90/10 and 99/1.

For the sake of clarity, by the expression "predominantly" it is meant that the mentioned stereoisomer or mixture of stereoisomers represents more than 90% of said compound (I), the remaining being obviously in the form of the other isomers.

As specific examples of the invention's compounds, one may cite, as non-limiting example, 4,8-cyclododecadien-1-one in the form of a mixture comprising about 99% w/w of (4E,8E)-4,8-cyclododecadien-1-one and about 1% w/w of the (4Z,8E)-4,8-cyclododecadien-1-one and (4E,8Z)-4,8-cyclododecadien-1-one stereoisomer (i.e. a 4,8-cyclododecadien-1-one in the form of a (E,E)/(E,Z) mixture 99/1 w/w, and also herein after referred to as "compound 1"). Said compound 1 possesses a unique odor having a variety of notes. In particular, said compound displays a woody/pin character as well as dry, musky and vetiver/earthy facets. The pin note is not terpenic but slightly aromatic, while the musky note reminds clearly of the nitro-musk notes by its powdery, sweet and earthy aspects.

As other example, one may cite 4,8-cyclododecadien-1-one in the form of a mixture comprising at least 90% w/w of (4E,8Z)-4,8-cyclododecadien-1-one and (4Z,8E)-4,8-cyclododecadien-1-one stereoisomers and about 5% w/w of the (4E,8E)-4,8-cyclododecadien-1-one stereoisomer (i.e. a 4,8-cyclododecadien-1-one in the form of a (E,E)/(E,Z) mixture of below 5/90 w/w, and also herein after referred to as "compound 2"). Said compound 2 has an odor similar to the one of the above described mixture but distinguishes itself by having a green note too and also by being more vetyver/earthy and aromatic, of the cardamom type.

These two ketones blend very favorably with any other musks or wood ingredients to impart a unique and unknown tonality by imparting an astonishing warmness and a richness of the fragrance.

As other specific, but non-limiting, examples of the invention's compounds, one may cite the following ones in Table 1:

TABLE 1

Invention's compounds and their odor properties and prior art compounds

| Compound structure and name | Odor notes |
| --- | --- |
| 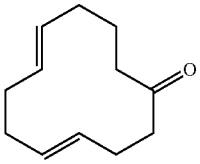 [SMILES: O=C1CC/C=C/CC/C=C/CCC1]<br>4,8-cyclododecadien-1-one in the form of a (E,E)/(E,Z) mixture | Woody, musky/aromatic as described above.<br>No aldehyde notes. |
| 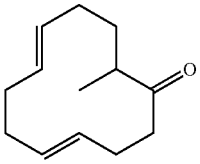<br>(4E,8E)-12-methylcyclododeca-4,8-dienone | Woody, musky/aromatic. Very similar to 4,8-cyclododecadien-1-one.<br>No aldehyde notes. |
| 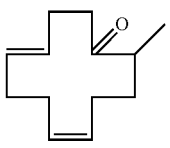<br>(4E,8Z)-12-methylcyclododeca-4,8-dienone | Woody, musky/aromatic. Very similar to 4,8-cyclododecadien-1-one but slightly weaker.<br>No aldehyde notes. |
| 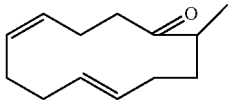<br>(4Z,8E)-12-methylcyclododeca-4,8-dienone | Woody, musky/aromatic. Very similar to 4,8-cyclododecadien-1-one but slightly weaker.<br>No aldehyde notes. |
| 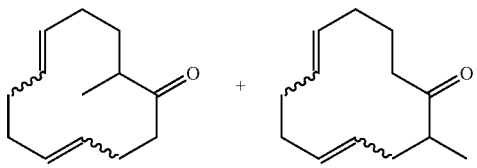<br>Mixture containing the various (Z,E) and (E,E) of isomers 12-methylcyclododeca-4,8-dienone and 2-methylcyclododeca-4,8-dienone | Woody, musky/aromatic. Very similar to 4,8-cyclododecadien-1-one but slightly weaker and more woody.<br>No aldehyde notes. |

TABLE 1-continued

Invention's compounds and their odor properties and prior art compounds

| Compound structure and name | Odor notes |
|---|---|
| 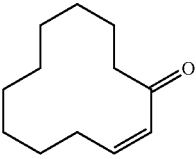<br>Cyclododec-2-en-1-one (see EP 115582) | Patchouli oil, no musk or aromatic notes. |
| 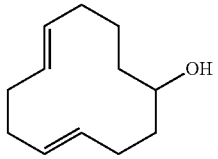 [SMILES: OC1CC/C=C/CC/C=C/CCC1]<br>5,9-cyclododecadien-1-ol (see US 3128304) | Natural amber, no musk or aromatic notes. |
| 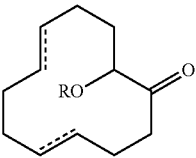<br>(see US 4990495) | All have aldehydic notes.<br>No musky odor. |

According to a particular embodiment of the invention, the compounds of formula (I) are (4E,8E)-4,8-cyclododecadien-1-one, (4Z,8E)-4,8-cyclododecadien-1-one, (4E,8Z)-4,8-cyclododecadien-1-one, (4E,8E)-12-methylcyclododeca-4,8-dienone, (4E,8Z)-12-methylcyclododeca-4,8-dienone, (4Z,8E)-12-methylcyclododeca-4,8-dienone, 2-methylcyclododeca-4,8-dienone and the mixtures thereof.

When the odor of the invention's compounds is compared with that of the prior art compounds, then the invention's compounds distinguish themselves by having a woody, aromatic and/or musky character and by lacking, or not possessing significant aldehyde notes, which are characteristic of some of the prior art compounds. Said differences lend the invention's compounds and the prior art compounds to be each suitable for different uses, i.e. to impart different organoleptic impressions.

The compounds of formula (I) as above described are novel compounds and therefore also an object of the present invention.

As mentioned above, the invention concerns the use of a compound of formula (I) as perfuming ingredient. In other words, it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs—und Geliermittel in Lebensmittel, Band 2 der Schriftenreihe Lebensmittelchemie, Lebensmittelqualität, Behr's VerlagGmbH &

Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

According to any one of the above embodiments of the invention, and in particular when the invention's compound is a 4,8-cyclododecadien-1-one mixture as defined above, at least one of said perfuming co-ingredient is a musk odorant. In particular said perfuming composition comprises:
i) as perfuming ingredient, at least one invention's compound as defined above;
ii) at least one perfuming co-ingredient having a woody and/or musk character; and
iii) optionally at least one perfumery adjuvant.

In particular said perfuming co-ingredient having a musk character can be selected amongst Exaltolide® (pentadecanolide; origin: Firmenich SA, Geneva, Switzerland), Habanolide® (pentadecenolide; origin: Firmenich SA, Geneva, Switzerland), Romandolide® ((1S,1'R)-[1-(3',3'-dimethyl-1'-cyclohexyl)ethoxycarbonyl]methyl propanoate; origin: Firmenich SA, Geneva, Switzerland), Helvetolide® ((1S,1'R)-2-[1-(3',3'-dimethyl-1'-cyclohexyl)ethoxy]-2-methylpropyl propanoate; origin: Firmenich SA, Geneva, Switzerland).

Indeed in such a case, it has been noticed that in such composition, the invention's compounds boost or impart an astonishing and clean nitro-musk and earthy effect, producing thus a synergetic effect in the direction of Tonalide ((5,6,7,8-tetrahydro-3,5,5,6,8,8-hexamethyl-2-naphtyl)-1-ethanone; origin: Givaudan SA, Vernier, Switzerland).

By "perfumery adjuvant" we mean here an ingredient capable of imparting additional added benefit such as a color, a particular light resistance, chemical stability, to etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that by "perfuming consumer product" it is meant a consumer product which is expected to deliver at least a perfuming effect, in other words it is a perfumed consumer product. For the sake of clarity, it has to be mentioned that by "perfumery consumer base" we mean here the functional formulation, as well as optionally additional benefit agents, corresponding to a consumer to product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 20% by weight, or even more, of the compounds of the invention based on the weight of the composition into which they are incorporated. Concentrations to lower than these, such as in the order of 0.1% to 10% by weight, can be used when these compounds are incorporated into perfumed articles, percentage being relative to the weight of the article.

The invention's compounds can be prepared according to the literature for the ketone or standard methods known in the art as described herein-below.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

1. Preparation of (E,E)-4,8-cyclododecadien-1-one (4E,8E)-13-oxabicyclo[10.1.0]trideca-4,8-diene To a mechanically stirred solution of E,E,E-1,4,8-cyclododecatriene (22.5 g, 139 mmol, available commercially from Alfa Aesar) in methylene chloride (200 ml) was added sodium bicarbonate (12 g, 139 mmol). The mixture was cooled to 0° C. and m-chloroperbenzoic acid (24 g, 166 mmol) was added in small portions over 2 hours. The reaction mixture was stirred at 0° C. for 1 hour, then allowed to warm to ambient temperature. Filtration, washing with sodium hydrogen sulphate (2 portions of 30 ml 10% aq. solution) and distillation of the methylene chloride solvent yielded the crude product. The crude product was dissolved in MTBE, washed with aqueous $NaHCO_3$, water and brine. The solvent was evaporated and the product (31.3 g; 30% starting material, 63% monoepoxide; 7% diepoxide) purified by distillation. The pure monoepoxide crystallised spontaneously (yield=79% taking into account recovered substrate).

$^1$H-NMR: 1.08-1.20 (m, 2H); 1.80-1.94 (m, 2H); 2.02-2.18 (m, 4H); 2.18-2.34 (m, 4H); 2.50-2.55 (d, 2H); 4.98-5.24 (m, 4H); 5.39-5.48 (m, 1H).

$^{13}$C NMR: 29.5 (t), 31.6 (t), 31.8 (t), 61.4 (d), 129.9 (d), 131.8 (d).

(E,E)-4,8-cyclododecadien-1-one

A mixture of lithium iodide (25 mg, 0.19 mmol) and the monoepoxide obtained above (1.05 g, 5.89 mmol) was heated to 200° C. After a few minutes, the brown reaction mixture was cooled to ambient temperature, mixed with aqueous sodium bicarbonate and extracted with MTBE. Washing with water, and brine, evaporation of the solvent and bulb to bulb distillation (Kugelrohr oven, 0.2 mbar, 90° C.) yielded the target ketone (0.8 g; 97% pure, yield=74%).

$^1$H-NMR: 1.15-1.24 (m, 2H); 1.95-2.08 (m, 6H); 2.24-2.43 (m, 6H); 5.00-5.18 (m, 4H).

$^{13}$C NMR: 18.9 (t), 28.9 (t), 32.0 (t), 32.2 (t), 33.1 (t), 41.5 (t), 42.9 (t), 128.9 (d), 130.9 (d), 131.4 (d), 133.1 (d), 210.7 (s);

2. Preparation of a Mixture of Isomers Containing the (E,Z)-4,8-cyclododecadien-1-one, (Z,E)-4,8-cyclododecadien-1-one the (E,E)-4,8-cyclododecadien-1-one Isomers To a mechanically stirred solution of (E,E)-4,8-cyclododecadien-1-one (10 g, 56 mmol) in n-propanol (50 ml) was added concentrated nitric acid (0.19 g, 60% aqueous). The mixture was heated to about 100° C. (reflux). After 7 hours of heating, an additional amount of concentrated nitric acid (0.05 g) was added and reflux continued for 16 hours. An additional amount of concentrated nitric acid (0.05 g) was added and the mixture was refluxed for another 44 hours.

The solvent was evaporated and the crude material (10.3 g) bulb to bulb distilled (Kugelrohr oven, 0.1 mbar, 90° C.). The yellow distillate (8.7 g, yield=87%) was washed with NaOH (5% aqueous) followed by brine, then redistilled (Vigreux distillation 0.2 mbar at 63° C.). The composition of the colorless distillate was 64% 4,8-E,E isomer; 23% 4-E, 8-Z isomer and 12% 4-Z, 8-E isomer.

The individual isomers were separated by careful distillation using a Fischer Spaltrohr™ column (vide infra).

Various mixtures with different ratios of each stereoisomers can be obtained by admixing the pure compounds.

a) The Pure (4E,8Z) Isomer (99%):

Separated by Fischer Spaltrohr™ distillation, 0.3 mbar, bp. 56.5° C. to The compound was further purified by recrystallisation from cold (−30° C.) pentane.

Mp=5.2° C.

Odor: woody, earthy, cardamon $^1$H-NMR: 1.65-1.75 (m, 2H); 1.95-2.05 (m, 6H); 2.30-2.50 (m, 6H); 5.15-5.35 (m, 4H).

$^{13}$C NMR: 21.4 (t), 24.7 (t), 27.4 (t), 28.7 (t), 31.5 (t), 40.5 (t), 40.7 (t), 127.8 (d), 129.7 (d), 131.0 (d), 131.9 (d), 211.8 (s);

b) The Pure (4Z,8E) Isomer (96%):

Prepared by Fischer Spaltrohr™ distillation, 0.27 mbar, bp. 56.6° C.

Odor: woody, earthy, weakly cardamon $^1$H-NMR: 1.60-1.65 (m, 2H); 1.98-2.13 (m, 6H); 2.28-2.42 (m, 4H); 2.45-2.51 (m, 2H); 5.08-5.23 (m, 2H); 5.28-5.33 (m, 1H); 5.39-5.48 (m, 1H).

$^{13}$C NMR: 19.6 (t), 24.0 (t), 27.5 (t), 31.0 (t), 31.7 (t), 40.5 (t), 43.1 (t), 129.9 (d), 129.9 (d), 130.0 (d), 131.3 (d), 211.2 (s);

Each single isomer can also be obtained as described above in section 1 by using the corresponding stereoisomer of the 1,4,8-cyclododecatriene.

3. Preparation of a mixture containing the various (Z,E) and (E,E) isomers of 12-methylcyclododeca-4,8-dienone and 2-methylcyclododeca-4,8-dienone Preparation of a mixture containing E,Z and E,E isomers of 2-methylcyclododeca-4,8-dienone and 12-methylcyclododeca-4,8-dienone To a cold (−70° C.) mechanically stirred mixture of diisopropylamine (12.07 g, 119 mmol) and THF (100 ml) under argon was added by syringe a solution of butyl lithium (70 ml, 1.6 molar in hexane). The mixture was allowed to warm up to 0° C., kept at this temperature for 30 min and then cooled down to −68°. Cyclododeca-4,8-dienone (20.1 g, 113 mmol; E,Z isomer mixture) was dissolved in THF (50 ml) and slowly added over 1 h. The mixture was allowed to warm to 0° C., then again cooled down to −72°. Methyl iodide (15.99 g, 113 mmol) was dissolved in THF (15 ml) and slowly added over 1 h. The mixture was allowed to warm to 20° C. and kept at this temperature overnight. Workup (reverse hydrolysis with ice/aqueous HCl, extraction with MTBE, washing with water, then brine, distillation of the solvent) followed by bulb to bulb distillation (Kugelrohr oven, 0.21 mbar, 70° C.) gave an odoriferous mixture (20.7 g). Flash-chromatography (heptane/ethyl acetate 98/2) using $SiO_2$ (345 g) allowed to separate the title mixture from to remaining starting material and dimethylated products.

The main isomers of 12-methylcyclododeca-4,8-dienone have been isolated by repeated careful Fischer Spaltrohr™ vacuum distillation.

(4E,8E)-12-methylcyclododeca-4,8-dienone

Bp 45.0° C./0.1 mbar.

$^1$H-NMR: 1.08-1.12 (d, 3H); 1.22-1.31 (m, 1H); 1.77-2.12 (m, 6H); 2.15-2.28 (m, 2H); 2.28-2.46 (m, 3H); 2.55-2.64 (m, 1H); 4.95-5.22 (m, 4H).

$^{13}$C NMR: 18.2 (q), 27.9 (t), 30.1 (t), 31.8 (t), 31.9 (t), 32.0 (t), 40.3 (t), 46.5 (d), 129.9 (d), 129.9 (d), 132.4 (d), 132.5 (d), 213.7 (s).

(4E,8Z)-12-methylcyclododeca-4,8-dienone

Bp 45.5° C./0.09 mbar.

$^1$H-NMR: 1.04-1.08 (d, 3H); 1.21-1.30 (m, 1H); 1.74-2.17 (m, 7H); 2.20-2.32 (m, 2H); 2.42-2.52 (m, 1H); 2.60-2.74 (m, 2H); 5.20-5.35 (m, 4H).

$^{13}$C NMR: 17.8 (q), 24.2 (t), 27.3 (t), 27.9 (t), 31.2 (t), 31.6 (t), 38.7 (t), 45.1 (d), 128.4 (d), 128.9 (d), 130.9 (d), 131.4 (d), 214.8 (s).

(4Z,8E)-12-methylcyclododeca-4,8-dienone

Bp 39.5° C./0.05 mbar.

$^1$H-NMR: 1.05-1.10 (d, 3H); 1.25-1.35 (m, 1H); 1.75-2.15 (m, 7H); 2.16-2.28 (m, 2H); 2.29-2.40 (m, 1H); 2.62-2.72 (m, 2H); 5.10-5.32 (m, 3H); 5.44-5.52 (m, 1H).

$^{13}$C NMR: 18.9 (q), 22.6 (t), 27.5 (t), 30.5 (t), 31.0 (t), 31.6 (t), 41.6 (t), 44.3 (d), 129.5 (d), 130.2 (d), 130.4 (d), 131.0 (d), 214.6 (s).

Example 2

Preparation of a Perfuming Composition

A perfuming composition for a man eau de Cologne was prepared by admixing the following ingredients:

| Parts by weight | Ingredient |
|---|---|
| 20 | Carbinol acetate |
| 20 | Geranyl acetate |
| 220 | Linalyl acetate |
| 200 | Bergamote essential oil |
| 30 | 10%* Raspberry ketone |
| 500 | Lemon essential oil |
| 80 | 4-cyclohexyl-2-methyl-2-butanol[1] |
| 120 | Exaltolide ® Total[2] |
| 80 | Crystal moss |
| 50 | 2-Methyl-4-(2,2,3-trimethyl-3-cyclopenten-1-yl)-4-penten-1-ol[1] |
| 80 | 10%* Galbanum essential oil |
| 100 | Clove essential oil |
| 40 | Helvetolide ®[3] |
| 50 | Hivernal ®[4] |
| 200 | Kephalis[5] |
| 200 | Lavander essential oil |
| 350 | Lyral ®[6] |
| 120 | Marjoram essential oil |
| 150 | Nutmeg essential oil |
| 100 | Benzyl salicylate |
| 200 | Sandela ®[7] |
| 220 | Sclareolate ®[8] |
| 20 | 2-Ethyl-4,4-dimethyl-l-cyclohexanone[1] |
| 500 | Vertofix ® Coeur [9] |
| 250 | (1S,2S,3S)-2,6,6-trimethyl-bicyclo[3.1.1]heptane-3-spiro-2'-cyclohexen-4'-on[1] |
| 100 | Ylang Extra |
| 4000 | |

*in dipropyleneglycol
[1] origin: Firmenich SA, Geneva, Switzerland
[2] pentadecanolide; origin: Firmenich SA, Geneva, Switzerland
[3] (1S,1'R)-2-[1-(3',3'-dimethyl-1'-cyclohexyl)ethoxy]-2-methylpropyl propanoate; origin: Firmenich SA, Geneva, Switzerland
[4] 3-(3,3/1,1-dimethyl-5-indanyl)propanal; origin: Firmenich SA, Geneva, Switzerland
[5] 4-(1-ethoxyethenyl)-3,3,5,5-tetramethyl-1-cyclohexanone; origin: Givaudan SA, Vernier, Switzerland
[6] 4/3-(4-hydroxy-4-methylpentyl)-3-cyclohexene-1-carbaldehyde; origin: International Flavors & Fragrances, USA
[7] 5-(2,2,3-trimethyl-3-cyclopentenyl)-3-methylpentan-2-ol; origin: Givaudan SA, Vernier, Switzerland
[8] propyl (S)-2-(1,1-dimethylpropoxy)propanoate; origin: Firmenich SA, Geneva, Switzerland
[9] methyl cedryl ketone; origin: International Flavors & Fragrances, USA The addition of 100 parts by weight of (E,E)-4,8-cyclododecadien-1-one to the above-described composition imparted to the latter a unique tonality and reinforced the masculine aspects by pushing the woody notes and providing a nitro-musk twist to the musky notes.

The addition of 100 parts by weight of a mixture of diastereoisomers containing about 90% w/w of (E,Z)-4,8-cyclododecadien-1-one and (Z,E)-4,8-cyclododecadien-1-one diastereoisomers and about 5% w/w of the (E,E)-4,8-cyclododecadien-1-one diastereoisomer imparted to the above composition an effect similar to the one imparted by (E,E)-4,8-cyclododecadien-1-one, but which was also more vetyver-earthy and reinforcing the green, aromatic/lavender tonalities.

Example 3

Preparation of a Perfuming Composition

A perfuming composition for a man eau de Cologne was prepared by admixing the following ingredients:

| Parts by weight | Ingredient |
|---|---|
| 10 | Styrallyl acetate |
| 70 | Hexylcinnamic aldehyde |
| 300 | Bergamote essential oil |
| 10 | 10%* Calone ®[1] |

-continued

| Parts by weight | Ingredient |
|---|---|
| 50 | 10%* Cis-3-Hexenol |
| 50 | Coriander essential oil |
| 10 | 1,1-Dimethyl-2-phenylethyl butanoate |
| 800 | Hedione ®[2] |
| 500 | Hedione ® HC[3] |
| 900 | 3-(1,3-benzodioxol-5-yl)-2-methylpropanal |
| 10 | 10%* Isobutylquinoleine |
| 40 | 10%* Isojasmone |
| 300 | Jasmal ®[4] |
| 20 | 10%* 2,6-Dimethyl-5-heptanal[5] |
| 20 | 10%* Nonenol |
| 20 | Trans-1-(2,2,6-trimethyl-1-cyclohexyl)-3-hexanol[5] |
| 30 | Oliban essential oil |
| 5 | Patchouli essential oil |
| 620 | Romandolide ®[6] |
| 20 | Rose essential oil |
| 310 | Benzyl salicylate |
| 40 | Cis-3-Hexenyl salicylate |
| 15 | Cis-3-Hexenyl tiglate |
| 50 | 10%* Gamma undecalactone |
| 200 | Vetyver Bourbon |
| 4400 | |

*in dipropyleneglycol
[1] 7-methyl-2H,4H-1,5-benzodioxepin-3-one; origin: Firmenich SA, Geneva, Switzerland
[2] methyl dihydrojasmonate; origin: Firmenich SA, Geneva, Switzerland
[3] methyl cis-dihydrojasmonate; origin: Firmenich SA, Geneva, Switzerland
[4] tetrahydro-3-pentyl-4(2h)-pyranyl acetate; origin: International Flavors & Fragrances, USA
[5] origin: Firmenich SA, Geneva, Switzerland
[6] (1S,1'R)-[1-(3',3'-dimethyl-1'-cyclohexyl)ethoxycarbonyl]methyl propanoate; origin: Firmenich SA, Geneva, Switzerland The addition of 200 parts by weight of (E,E)-4,8-cyclododecadien-1-one to the above-described composition imparted to the latter a reinforced vetyver aspect and imparted a woody/pin, musky twist which boosted the masculine connotation of the fragrance.

The addition of 100 parts by weight of a mixture of diastereoisomers containing about 90% w/w of (E,Z)-4,8-cyclododecadien-1-one and (Z,E)-4,8-cyclododecadien-1-one diastereoisomers and about 5% w/w of the (E,E)-4,8-cyclododecadien-1-one diastereoisomer imparted to the above composition an effect clearly more rooty/earthy vetyver and slightly less musky than the addition of (E,E)-4,8-cyclododecadien-1-one above described.

Example 4

Preparation of a Perfuming Composition

A perfuming composition of the musk type was prepared by admixing the following ingredients:

| Parts by weight | Ingredient |
|---|---|
| 30 | 8-Methoxy-2,6,6,8-tetramethyl-tricyclo[5.3.1.0(1,5)]undecane |
| 5170 | Dipropylene glycol |
| 300 | Habanolide ®[2] |
| 600 | Helvetolide ®[3] |
| 200 | Muscenone ™ Delta[4] |
| 6300 | |

[1] pentadecenolide; origin: Firmenich SA, Geneva, Switzerland
[2] (1S,1'R)-2-[1-(3',3'-dimethyl-1'-cyclohexyl)ethoxy]-2-methylpropyl propanoate; origin: Firmenich SA, Geneva, Switzerland
[3] 3-methyl-(4/5)-cyclopentadecenone; origin: Firmenich SA, Geneva, Switzerland The addition of 1000 parts by weight of (E,E)-4,8-cyclododecadien-1-one to the above-described composition imparted to the latter an astonishing reminiscence of the nitro-musk notes.

The addition of 1000 parts by weight of a mixture of diastereoisomers containing about 90% w/w of (E,Z)-4,8-cyclododecadien-1-one and (Z,E)-4,8-cyclododecadien-1-one diastereoisomers and about 5% w/w of the (E,E)-4,8-cyclododecadien-1-one diastereoisomer boosted the earthy aspects, providing thus an astonishing reminiscence of the aromatic polycyclic musks which are nowadays strongly limited in use.

What is claimed is:

1. A method to confer, enhance, improve or modify the odor properties of a perfuming composition or of a perfumed article, which method comprises adding to said composition or article an effective amount of at least one compound of formula (I) to provide a woody, aromatic and/or musky character to said composition or article without providing significant aldehyde notes, wherein the at least one compound of formula (I) is:

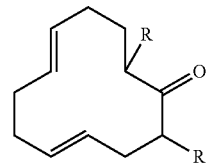

(I)

wherein one R group is a hydrogen atom and the other is a hydrogen atom or a $C_{1-3}$ alkyl group; and
each carbon-carbon double bond of said compound, independently from each other, can be in a configuration Z or E or a mixture thereof.

2. A perfuming composition comprising
i) the at least one compound of formula (I) according to claim 1;
ii) at least one ingredient selected from the group consisting of a perfumery carrier and a perfumery base; and
iii) optionally at least one perfumery adjuvant.

3. A perfuming composition according to claim 2, wherein said perfumery base comprises at least one perfuming co-ingredient having a woody and/or musk character.

4. A perfuming composition according to claim 2, wherein the at least one compound of formula (I) is in the form of a mixture of stereoisomers (4E,8E), (4Z,8E) and (4E,8Z), wherein the w/w ratio (4E,8E)/[(4Z,8E) +(4E,8Z)] is comprised between 20/80 and 1/99, or between 80/20 and 99.5/0.5.

5. A perfuming composition according to claim 2, wherein the at least one compound of formula (I) is (E,E)-4,8-cyclododecadien-1-one, (Z,E)-4,8-cyclododecadien-1-one, (E,Z)-4,8-cyclododecadien1-one, (4E,8E)-12- methylcyclododeca-4,8-dienone, (4E,8Z)-12-methylcyclododeca-4,8-dienone, (4Z,8E)-12- methylcyclododeca-4,8-dienone, 2-methylcyclododeca-4,8-dienone and the mixtures thereof.

6. A perfuming consumer product comprising:
i) the at least one compound of formula (I) according to claim 1; and
ii) a perfumery consumer base.

7. A perfuming consumer product according to claim 6, wherein the perfumery consumer base is a perfume, a fabric care product, and a body-care product, an air care product or a home care product.

8. A perfuming consumer product according to claim 6, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

9. The method of claim 1 wherein the at least one compound of formula (I) is added to a perfuming composition that includes at least one ingredient selected from the group consisting of a perfumery carrier and a perfumery base; and optionally at least one perfumery adjuvant.

10. The method according to claim 9, wherein said perfumery base comprises at least one perfuming co-ingredient having a woody and/or musk character.

11. The method of claim 1 wherein the at least one compound of formula (I) is added to a perfuming consumer product comprising a perfumery consumer base.

12. The method according to claim 11, wherein the perfumery consumer base is a perfume, a fabric care product, and a body-care product, an air care product or a home care product.

13. The method according to claim 11, wherein the perfumery consumer base is a fine perfume, a cologne, an aftershave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

14. The method according to claim 1, wherein one R group is a hydrogen atom and the other is a hydrogen atom or a methyl or ethyl group.

15. The method according to claim 1, wherein the at least one compound of formula (I) is in the form of a mixture of stereoisomers (4E,8E), (4Z,8E) and (4E,8Z), wherein the w/w ratio (4E,8E)/[(4Z,8E)+(4E,8Z)] is comprised between 20/80 and 1/99, or between 80/20 and 99.5/0.5.

16. The method according to claim 1, wherein the at least one compound of formula (I) is (E,E)-4,8-cyclododecadien-1-one, (Z,E)-4,8-cyclododecadien-1-one, (E,Z)-4,8-cyclododecadien-1-one, (4E,8E)-12- methylcyclododeca-4,8-dienone, (4E,8Z)-12-methylcyclododeca-4,8-dienone, (4Z,8E)-12- methylcyclododeca-4,8-dienone, 2-methylcyclododeca-4,8-dienone and the mixtures thereof.

* * * * *